(12) United States Patent
Schlaeper et al.

(10) Patent No.: US 10,543,353 B2
(45) Date of Patent: Jan. 28, 2020

(54) BLOOD FLOW REVERSAL VALVES AND RELATED SYSTEMS AND METHODS

(71) Applicants: Fresenius Medical Care Holdings, Inc., Waltham, MA (US); Fresenius Medical Care Deutschland GmbH, Bad Homburg (DE)

(72) Inventors: Christian Schlaeper, Wehrheim (DE); Harald Peter, Schweinfurt (DE); Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 650 days.

(21) Appl. No.: 15/230,561

(22) Filed: Aug. 8, 2016

(65) Prior Publication Data

US 2016/0354597 A1 Dec. 8, 2016

Related U.S. Application Data

(62) Division of application No. 13/785,537, filed on Mar. 5, 2013, now Pat. No. 9,415,151.
(Continued)

(51) Int. Cl.
*A61M 39/22* (2006.01)
*A61M 1/30* (2006.01)
(Continued)

(52) U.S. Cl.
CPC ............ *A61M 39/223* (2013.01); *A61M 1/30* (2013.01); *A61M 1/367* (2013.01); *F16K 11/074* (2013.01); *A61M 2039/226* (2013.01)

(58) Field of Classification Search
CPC ....... A61M 39/223; A61M 1/30; A61M 1/367
See application file for complete search history.

(56) References Cited

U.S. PATENT DOCUMENTS 3,157,201 A 11/1964 Littmann
3,626,938 A 12/1971 Versaci
(Continued)

FOREIGN PATENT DOCUMENTS

DE 19528907 11/1996
EP 1106191 6/2001
(Continued)

OTHER PUBLICATIONS

Mercadal et al., Determination of Access Blood Flow From Ionic Dialysance: Theory and Validation, Kidney Int'l, vol. 56 (1999), pp. 1560-1565.
(Continued)

*Primary Examiner* — Tatyana Zalukaeva
*Assistant Examiner* — Sara A Sass
(74) *Attorney, Agent, or Firm* — Fish & Richardson P.C.

(57) ABSTRACT

This disclosure relates to methods of reversing blood flow using a blood flow reversal valve that includes a first member having a first passage and a second passage, and a second member having a first passage and a second passage. The first and second members are rotatably fixed relative to one another such that the first passage of the first member is aligned with the first passage of the second member and the second passage of the first member is aligned with the second passage of the second member. A flow directing element is disposed in the cavity and is moveable between a first position in which the first passage of the first member and the first passage of the second member are fluidly connected and a second position in which the first passage of the first member and the second passage of the second member are fluidly connected.

8 Claims, 9 Drawing Sheets

Related U.S. Application Data

(60) Provisional application No. 61/705,411, filed on Sep. 25, 2012.

(51) Int. Cl.
*A61M 1/36* (2006.01)
*F16K 11/074* (2006.01)

(56) References Cited

U.S. PATENT DOCUMENTS

| | | | |
|---|---|---|---|
| 4,397,335 A | 8/1983 | Doblar et al. | |
| 4,695,385 A | 9/1987 | Boag | |
| 4,821,996 A | 4/1989 | Bellotti et al. | |
| 4,885,087 A | 12/1989 | Kopf | |
| 4,898,669 A | 2/1990 | Tesio | |
| 4,904,245 A | 2/1990 | Chen et al. | |
| 5,082,025 A | 1/1992 | DeVries et al. | |
| 5,135,026 A | 8/1992 | Manska | |
| 5,172,725 A * | 12/1992 | Kitagawa | F16K 11/0856 137/625.43 |
| 5,392,772 A | 2/1995 | Zilbershtein | |
| 5,605,630 A | 2/1997 | Shibata | |
| 5,685,989 A | 11/1997 | Krivitski et al. | |
| 5,830,365 A | 11/1998 | Schneditz | |
| 5,894,011 A | 4/1999 | Prosl et al. | |
| 6,058,974 A * | 5/2000 | Blomgren | F16K 11/074 137/625.43 |
| 6,177,049 B1 | 1/2001 | Schnell et al. | |
| 6,308,737 B1 | 10/2001 | Krivitski | |
| 6,319,465 B1 | 11/2001 | Schnell et al. | |
| 6,572,576 B2 * | 6/2003 | Brugger | A61M 1/3626 210/646 |
| 6,596,234 B1 | 7/2003 | Schnell et al. | |
| 6,695,807 B2 | 2/2004 | Bell et al. | |
| 6,726,647 B1 | 4/2004 | Sternby et al. | |
| 6,726,663 B1 | 4/2004 | Dennis | |
| 7,384,543 B2 | 6/2008 | Jonsson et al. | |
| 2001/0031222 A1 * | 10/2001 | Schnell | A61M 1/367 422/400 |
| 2003/0018290 A1 | 1/2003 | Brugger et al. | |
| 2003/0138348 A1 | 7/2003 | Bell et al. | |
| 2005/0145549 A1 | 7/2005 | Jonsson et al. | |
| 2005/0178732 A1 | 8/2005 | Krivitski et al. | |
| 2007/0173753 A1 | 7/2007 | Paul | |
| 2014/0048161 A1 | 2/2014 | Sternby et al. | |

FOREIGN PATENT DOCUMENTS

| | | |
|---|---|---|
| EP | 2168611 | 11/2011 |
| WO | 9964088 | 12/1999 |
| WO | WO2005046439 | 5/2005 |
| WO | WO200505061043 | 7/2005 |
| WO | WO2009001152 | 12/2008 |

OTHER PUBLICATIONS

Nikolai M. Krivitski, Novel Method to Measure Access Flow During Hemodialysis by Ultrasound Velocity Dilution Technique, ASAIO Journal, Jul.-Sep. 1995, vol. 41, No. 3 at M741.

Paul G. Sakiewicz, Emil P. Paganni, and Eugene Wright, Introduction of a Switch that Can Reverse Blood Flow Direction On-Line during Hemodialysis, ASAIO Journal 2000 at 464.

Thomas A. Depner and Nikolai M. Krivitski, Clinical Measurement of Blood Flow in Hemodialysis Access Fistulae and Grafts by Ultrasound Dilution, ASAIO Journal, Jul.-Sep. 1995, vol. 41, No. 3 at M745.

Thomas A. Depner, Nikolai M. Krivitski, and David MacGibbon, Hemodialysis Access Recirculation Measured by Ultrasound Dilution, ASAIO Journal, Jul.-Sep. 1995, vol. 41, No. 3 at M749.

Fresenius Combilines with Access Flow Reversing Connector 510(k) Submission; 2002.

"Reverso Flow Reversing Interconnector" Brochure, Medisystems HemoDYNAMIC Devices, 2000.

Notification of Transmittal of the International Search Report and the Written Opinion of the International Search Authority from corresponding PCT Application PCT/US2013/061285, dated Mar. 5, 2014, 16 pages.

Notification Concerning Transmittal of the International Preliminary Report on Patentability for corresponding PCT Application PCT/US2013/061285, dated Apr. 9, 2015, 10 pages.

* cited by examiner

BLOOD FLOW REVERSAL VALVES AND RELATED SYSTEMS AND METHODS

CROSS-REFERENCE TO RELATED APPLICATIONS

This is a divisional application and claims the benefit of U.S. application Ser. No. 13/785,537 filed Mar. 3, 2013, which claims the benefit of U.S. Application Ser. No. 61/705,411, filed on Sep. 25, 2012. Both of these priority applications are incorporated by reference herein.

TECHNICAL FIELD

This invention relates to blood flow reversal valves and related systems and methods.

BACKGROUND

Many modern medical procedures use tubing sets of varying complexity to withdraw fluid from a patient, or to administer fluid to a patient, or to do both. One example of such a procedure is hemodialysis. In hemodialysis, the patient's blood is cleansed by drawing it out of the patient through a blood access site, typically via a catheter, and passing it through an artificial kidney (often called a "dialyzer"). The artificial kidney includes a semi-permeable membrane which removes impurities and toxins by a process of diffusion. The purified blood is then returned to the patient. An extracorporeal circuit including a pump and hemodialysis tubing set is typically used to transport the blood between the blood access site and the artificial kidney.

Many of the tubing sets used in medical procedures involving extracorporeal treatment of fluid, such as hemodialysis, are configured so that fluid can flow through the system in a desired direction during the medical procedure. A pumping device can be used to control the fluid flow rate in the system. In hemodialysis, for example, a peristaltic pump is typically used to draw blood from the patient and move the blood through the tubing set during the treatment procedure. During hemodialysis, blood is initially drawn from the patient's blood access (e.g., a vein or an artery, but more typically an arteriovenous graft or fistula) and flows through a series of connected tubing segments to the artificial kidney for cleansing. After passing through the artificial kidney, the blood then flows through other tubing segments that return the blood to the patient. Thus, there is generally a continuous circuit of blood flowing from the patient, through the artificial kidney, and then back to the patient during treatment.

During hemodialysis, blood is generally drawn from an upstream position in the blood access and then returned to a downstream position in the blood access. However, it has been found to be advantageous, for limited time periods, to reverse the direction that blood is received from and returned to the patient during hemodialysis. When the blood flow is reversed, blood is initially drawn from a downstream position in the blood access. The blood then flows through tubing segments to the artificial kidney for treatment before it is returned to the upstream position in the blood access. Typically this procedure is carried out by trained clinical personnel, e.g., dialysis clinicians. When the blood flow is reversed, any of various parameters, such as blood access flow rate, can be measured or derived from measurements. The data can provide useful information about the patient's condition and the effectiveness of the treatment. For example, practitioners can use information gathered during periods of reversed blood flow to evaluate the condition of the blood access, to get advanced warning on other health problems, such as access restrictions, and to prescribe preventive measures, such as blood access revision or replacements, which are generally needed after a few years of continuous dialysis.

SUMMARY

In one aspect of the invention, a blood flow reversal valve includes a first member having a first passage and a second passage and a second member having a first passage and a second passage. The first and second members are rotatably fixed relative to one another such that the first passage of the first member is aligned with the first passage of the second member and the second passage of the first member is aligned with the second passage of the second member. A flow directing element is disposed in a cavity formed between the first and second members. The flow directing element is moveable relative to the first and second members between a first position in which the first passage of the first member and the first passage of the second member are fluidly connected and the second passage of the first member and the second passage of the second member are fluidly connected, and a second position in which the first passage of the first member and the second passage of the second member are fluidly connected and the second passage of the first member and the first passage of the second member are fluidly connected.

In another aspect of the invention, a blood treatment system includes a blood flow reversal valve including a first member having a first passage and a second passage and a second member having a first passage and a second passage. The first and second members are rotatably fixed relative to one another such that the first passage of the first member is aligned with the first passage of the second member and the second passage of the first member is aligned with the second passage of the second member. A flow directing element of the blood flow reversal valve is disposed in a cavity formed between the first and second members, the flow directing element being moveable relative to the first and second members between a first position in which the first passage of the first member and the first passage of the second member are fluidly connected and the second passage of the first member and the second passage of the second member are fluidly connected, and a second position in which the first passage of the first member and the second passage of the second member are fluidly connected and the second passage of the first member and the first passage of the second member are fluidly connected. The system further includes a blood treatment device including a valve retention element configured to secure the blood flow reversal valve to the blood treatment device and an actuator configured to move the flow directing element of the blood flow reversal valve from the first position to the second position.

In an additional aspect of the invention, a method of reversing blood flow uses a blood flow reversal valve that includes a first member having a first passage and a second passage, a second member rotationally fixed relative to the first member and having a first passage and a second passage, and a flow directing element disposed in a cavity formed between the first and second members. The method includes moving the flow directing element of the blood flow reversal valve from a first position in which the first passage of the first member and the first passage of the second member are fluidly connected and the second passage of the first member and the second passage of the second member are fluidly connected to a second position in which the first passage of the first member and the second passage of the second member are fluidly connected and the second passage of the first member and the first passage of the second member are fluidly connected. The first and second members of the blood flow reversal valve remain fixed with respect to one another while the flow directing element moves from the first position to the second position.

Implementations can include one or more of the following features.

In some implementations, the flow directing element is rotatable about a longitudinal axis of the blood flow reversal valve.

In certain implementations, the first passages are aligned along an axis that is substantially parallel to the longitudinal axis, and the second passages are aligned along an axis that is substantially parallel to the longitudinal axis.

In some implementations, the flow directing element defines a first flow path and a second flow path.

In certain implementations, the first flow path fluidly connects the first passage of the first member to the first passage of the second member and the second flow path fluidly connects the second passage of the first member to the second passage of the second member when the flow directing element is in the first position.

In some implementations, the first flow path fluidly connects the second passage of the first member to the first passage of the second member and the second flow path fluidly connects the first passage of the first member to the second passage of the second member when the flow directing element is in the second position.

In certain implementations, the flow directing element is substantially cylindrical.

In some implementations, the first and second flow paths are substantially semi-helical.

In certain implementations, each of the first and second flow paths has a kidney-shaped cross-sectional area.

In some implementations, the flow directing element includes a body defining a central lumen and a partition extending through the lumen to form the first and second flow paths.

In certain implementations, the partition extends along a curved path between a first end of the body and a second end of the body.

In some implementations, the partition extends along a substantially semi-helical path between the first end of the body and the second end of the body.

In certain implementations, each of the first and second flow paths has a substantially half-circular cross-sectional area.

In some implementations, the partition twists by about 5 degrees to about 180 degrees from a first end of the body to a second end of the body.

In certain implementations, the partition twists by about 90 degrees from the first end of the body to the second end of the body.

In some implementations, the blood flow reversal valve further includes a projection that extends radially from the flow directing element.

In certain implementations, the projection extends through a slot that is defined by at least one of the first and second members.

In certain implementations, the first and second members cooperate to define the slot.

In some implementations, the slot extends circumferentially about the first and second members.

In certain implementations, the projection extends radially a sufficient distance to engage an actuator of a blood treatment machine when the blood flow reversal valve is connected to the blood treatment machine.

In some implementations, the valve retention element includes resilient fingers configured to releasably engage fluid line connectors of the blood flow reversal valve.

In certain implementations, the actuator defines an opening configured to receive a projection that extends radially from the flow directing element of the blood flow reversal valve.

In some implementations, the actuator is configured to rotate the flow directing element.

In certain implementations, the blood treatment system further includes a controller programmed to move the actuator.

In some implementations, the controller is programmed to move the actuator at a predetermined time during a blood treatment.

In certain implementations, moving the flow directing element from the first position to the second position includes rotating the flow directing element relative to first and second members.

In some implementations, the flow directing element is moved from the first position to the second position by an actuator of a blood treatment machine.

In certain implementations, the method further includes transmitting a signal from a controller of the blood treatment machine to the actuator to move the flow directing element.

In some implementations, the method further includes moving the flow directing element from the second position back to the first position.

In certain implementations, the method further includes running a blood pump to force blood through the blood flow reversal valve.

In some implementations, the method further includes stopping the blood pump prior to rotating the flow directing element from the first position to the second position.

In certain implementations, the method further includes measuring one or more parameters of blood flowing through the blood flow reversal valve.

Implementations can include one or more of the following advantages.

Blood flow reversal valves described herein can advantageously reverse the blood flow through fluid lines connected thereto without requiring repositioning or twisting of the fluid lines relative to one another. Reduced repositioning or twisting of the fluid lines can result in less kinking or binding of the fluid lines and, as a result, better flow through the fluid lines.

Certain blood flow reversal valves described herein can be connected to a blood treatment machine (e.g., a hemodialysis machine) for automatically reversing blood flow. As a result, blood flow reversal can be achieved more easily with automated blood flow reversal valves described herein than with certain manually operated blood flow reversal valves. Additionally, the system (e.g., a control unit or processor of the system) can be programmed to automatically reverse blood flow and take measurements at designated times throughout the treatment. As a result, such measurements can be taken at the ideal times throughout the treatment even if a clinician is not present to manually reverse the blood flow.

The details of one or more embodiments are set forth in the accompanying drawings and the description below. Other aspects, features, and advantages will be apparent from the description and drawings, and from the claims.

DETAILED DESCRIPTION

Figure 1:
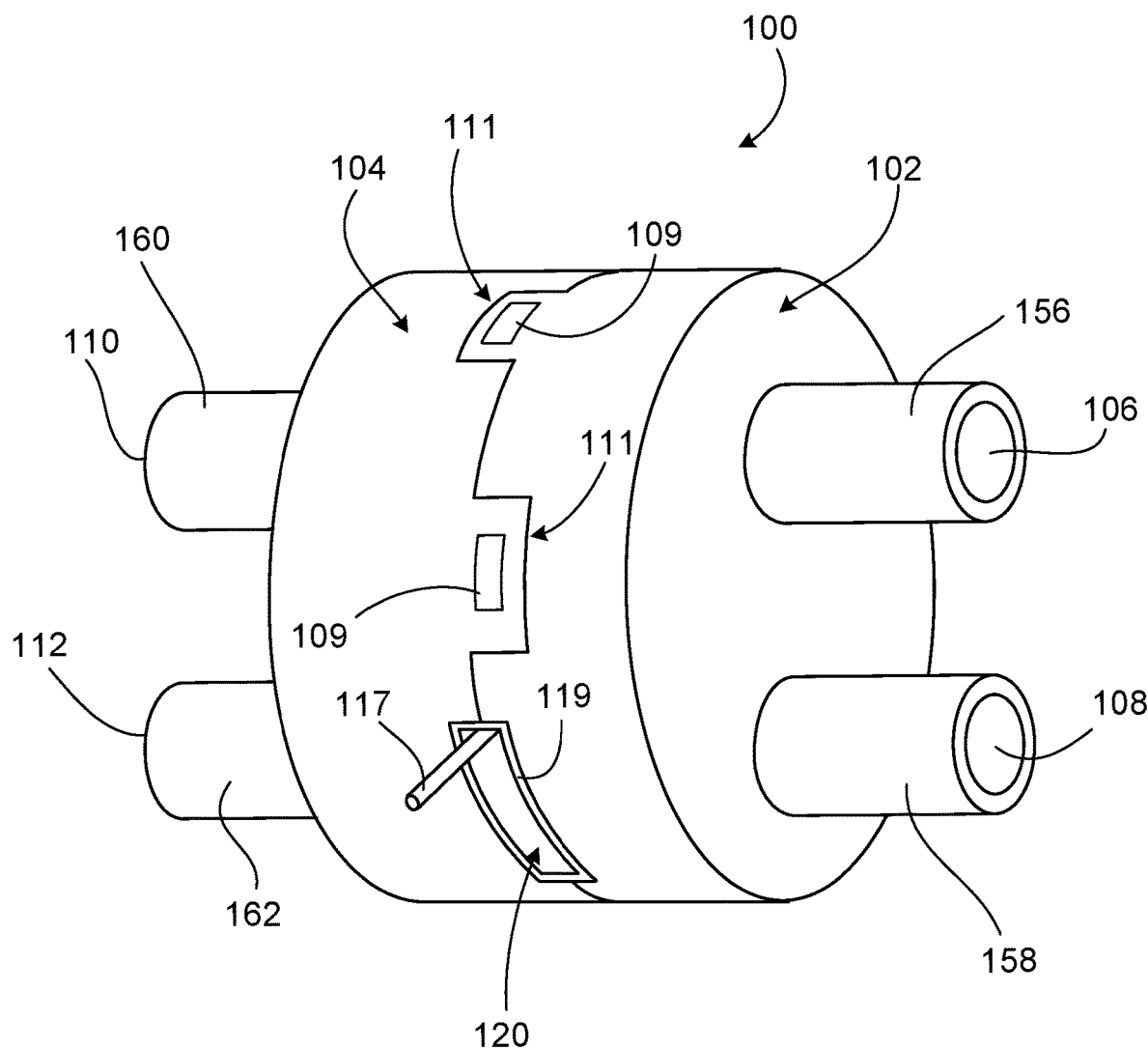
FIG. 1 is a perspective view of a blood flow reversal valve.
Figure 2:
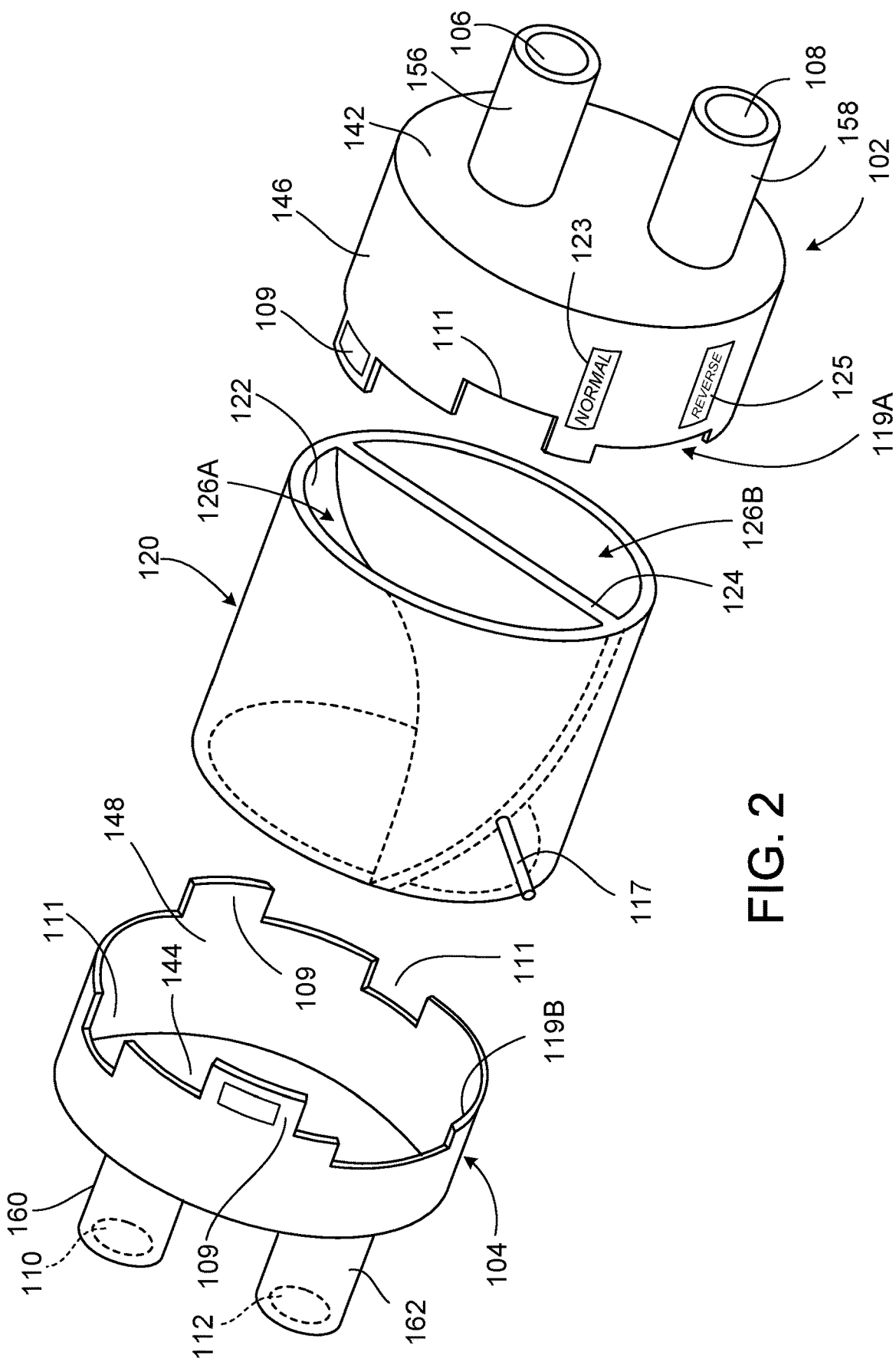
FIG. 2 is an exploded, perspective view of the blood flow reversal valve of FIG. 1.

Referring to FIGS. 1 and 2, a blood flow reversal valve 100 includes a generally cylindrical first valve body 102, a generally cylindrical second valve body 104, and a central rotatable flow directing element 120 disposed in a cavity 105 (shown in FIGS. 3 and 4) formed between the first and second valve bodies 102, 104. As shown in FIG. 2, the first valve body 102 and the second valve body 104 are formed of generally disk-shaped end plates 142, 144 and circumferentially formed cylindrical walls 146, 148 that extend from the end plates 142, 144. The first and second valve bodies 102, 104 are axially and rotationally fixed relative to one another, and the flow directing element 120 is rotatable within the cavity 105.

The first and second valve bodies 102, 104 are secured to one another by mating features in the form of tabs 109 and slots 111 that are formed around respective adjoining edges of the first and second valve bodies 102, 104 and are spaced to align with one another for assembly of the blood flow reversal valve 100. The tabs 109 and slots 111 are configured to be pressed into and coupled to one another. For example, the tabs 109 and slots 111 can include snap-in style detents, resilient fingers that deflect and lock in place to connect the first and second valve bodies 102, 104, or other interlocking features and elements to secure the valve bodies 102, 104 together.

Still referring to FIGS. 1 and 2, the first valve body 102 includes blood line connectors 156, 158 that extend outwardly from the end plate 142, and the second valve body 104 includes blood line connectors 160, 162 that extend outwardly from the end plate 144. Fluid passages 106, 108, 110, 112 extend through the blood line connectors 156, 158, 160, 162 and the end plates 142, 144 to provide fluid communication with the central cavity 105 of the valve 100. Because the first and second valve bodies 102, 104 are rotationally fixed relative to one another, the blood line connectors 156 and 160 are fixed in axial alignment with one another, and the blood line connectors 158 and 162 are fixed in axial alignment with one another. As a result, the fluid passages 106 and 110 are axially aligned with one another, and the fluid passages 108, 112 are axially aligned with one another. However, as will be described below, the flow directing element 120 can be rotationally positioned to either fluidly connect the axially aligned fluid passage pairs (106/110 and 108/112) of the first and second valve bodies 102, 104 or to fluidly connect the axially misaligned fluid passage pairs (106/112 and 108/110) of the first and second valve bodies 102, 104.

As shown in FIG. 2, the first valve body 102 includes a first slot portion 119A and the second valve body 104 includes a second slot portion 119B. The first and second slot portions 119A, 119B axially align with one another when the first and second valve bodies 102, 104 are secured to one another, as shown in FIG. 1, to form a slot 119. A pin 117 is secured to the flow directing element 120 and extends radially outward through the slot 119. The pin 117 can be moved along the slot 119 in order to rotate the flow directing element 120 from a first position that causes blood to flow through the valve 100 in a normal direction to a second position that causes blood to flow through the valve 100 in a reverse direction.

As shown in FIG. 2, the first valve body 102 includes visual indicators 123, 125 that are used to indicate the orientation of the flow directing element 120 relative to the first and second valve bodies 102, 104. Specifically, the visual indicators 123, 125 include the words "Normal" and "Reverse," respectively, applied (e.g., printed, engraved, molded, applied using stickers, or applied by other suitable methods) to portions of the cylindrical wall 146 that are adjacent opposite end regions of the slot 119. As a result, the user can easily determine that the flow directing element 120 is in the normal flow position when the pin 117 is adjacent the indicator 123 and can easily determine that the flow directing element 120 is in the reverse flow position when the pin 117 is adjacent the indicator 125.

Blood lines (e.g., tubing from a blood line set) can be connected to the blood line connectors 156, 158, 160, 162. For example, the blood lines can be slid over the blood line connectors 156, 158, 160, 162 and secured (e.g., adhesively attached) to the blood line connectors 156, 158, 160, 162. In some implementations, the blood lines are attached to their associated blood line connectors by applying a solvent, such as cyclohexanone, to the blood line connectors and then sliding the blood lines over the blood line connectors.

Referring to FIG. 2, the central rotatable flow directing element 120 is arranged and configured to rotate about a longitudinal axis 115 of the flow reversal valve 100 to direct flow in a desired manner between the fluid passages 106, 108 of the first valve body 102 and the fluid passages 110, 112 of the second valve body 104. The rotatable flow directing element 120 is formed of a cylindrical outer wall 122 forming an inner flow cavity, and an inner, semi-helical partition 124 that divides the inner flow cavity into a first flow path 126A and a second flow path 126B. The partition 124 is twisted about the longitudinal axis 115 to form the semi-helical profile. As a result of this configuration, the first flow path 126A and the second flow path 126B follow twisted, curved profiles. The partition 124 typically has a smooth, gradual surface that twists along the semi-helical profile. The first flow path 126A and the second flow path 126B are substantially the same shape and size, and follow similarly orientated paths through the flow directing element 120.

Figure 3:
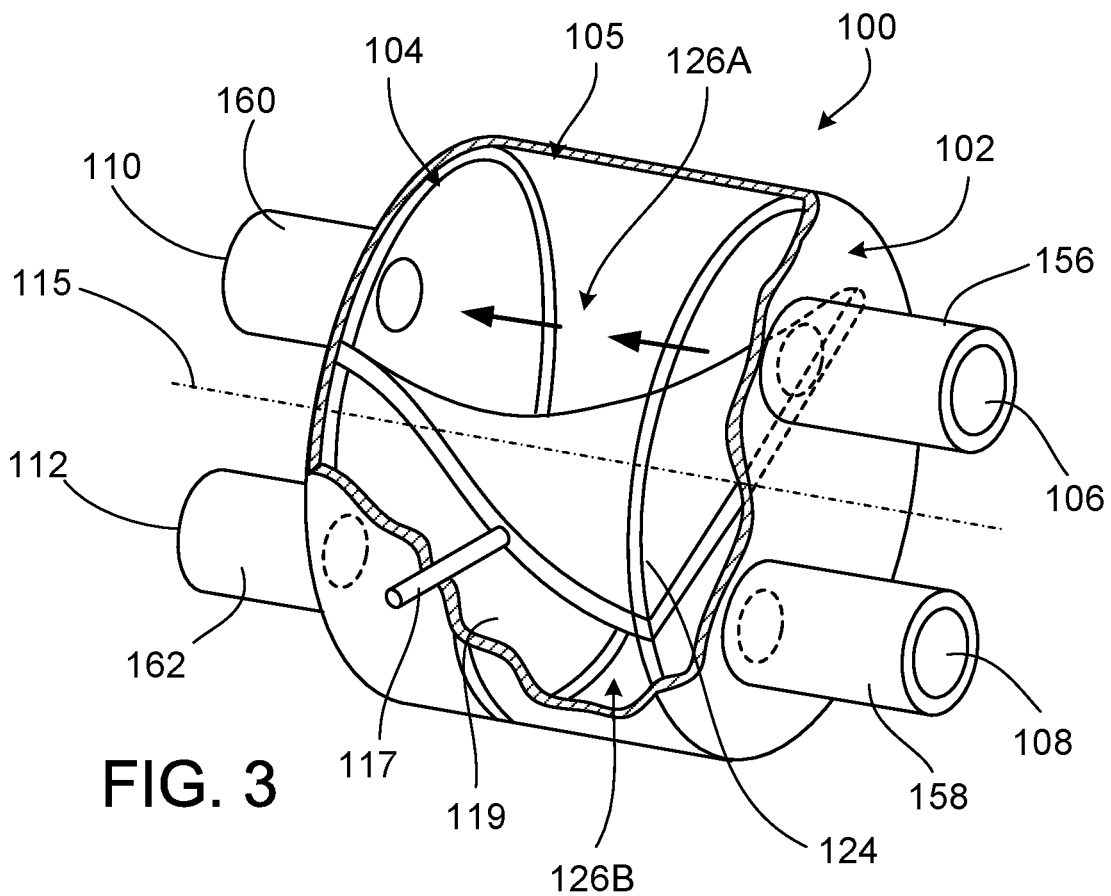
FIGS. 3 and 4 are cutaway, perspective views of the blood flow reversal valve of FIG. 1 with a central flow directing element of the valve in first and second positions, respectively, to direct flow in a normal direction and in a reverse direction, respectively.
Figure 4:
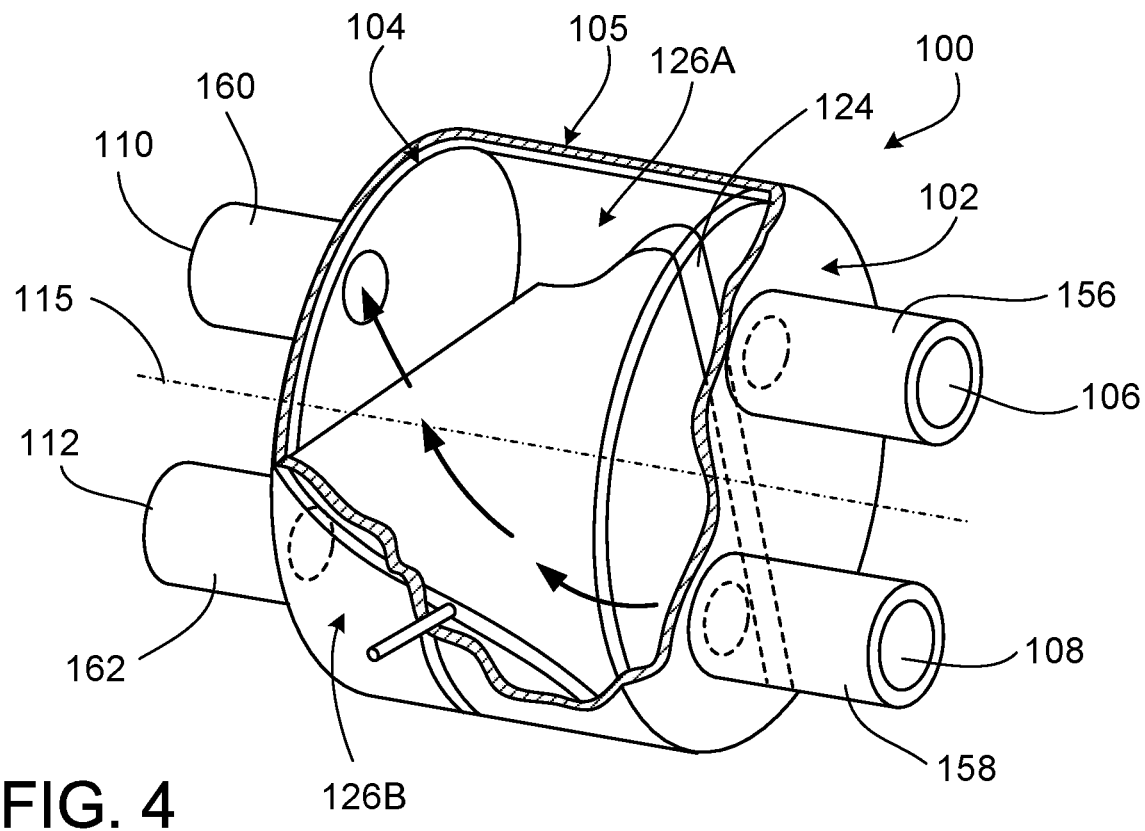

Along its axial length, the partition 124 rotates or twists at an angle that allows the axially aligned fluid passages 106 and 110 and the axially aligned fluid passages 108 and 112 to be fluidly connected when the flow directing element is in the normal flow orientation (shown in FIG. 3) and that allows the axially misaligned fluid passages 106 and 112 and the axially misaligned fluid passages 108 and 110 to be fluidly connected when the flow directing element is in the reverse flow orientation (shown in FIG. 4). Specifically, when the flow directing element 120 is in the normal flow orientation, the flow path 126A connects the fluid passage 106 to the fluid passage 110 and the flow path 126B connects the fluid passage 108 to the fluid passage 112. When the flow directing element 120 is in the reverse flow orientation, the flow path 126B connects the fluid passage 106 to the fluid passage 112 and the flow path 126A connects the fluid passage 108 to the fluid passage 110. Since the first and second flow paths 126A, 126B are semi-circular and extend circumferentially almost 180 degrees within the cylindrical outer wall 122 of the flow directing element 120, the twist angle of the partition 124 typically only needs to be large enough to overcome the width of the fluid passages, as well as the width of the partition 124. For example, the partition twist angle can be about 5 degrees to about 180 degrees (e.g., about 60 degrees to about 120 degrees, about 90 degrees).

The distance that the flow directing element 120 needs to be rotated in order to reverse blood flow through the valve is dependent on the twist angle of the partition 124 and the arrangement of the fluid passages. As the twist angle increases, the rotational travel distance required to reverse blood flow through the valve 100 will also increase. Typically, the partition 124 is configured so that rotating the flow directing element 120 by about 5 degrees to about 180 degrees (e.g., about 60 degrees to about 120 degrees, about 90 degrees) about the longitudinal axis 115 is sufficient to reverse the blood flow.

The flow directing element 120 is sized to create a press-fit type seal within the cavity 105 between the first and second valve bodies 102, 104 when the first and second valve bodies 102, 104 are secured to one another. For example, the flow directing element 120 can have an axial length that is greater than or equal to the axial length of the cavity 105. In addition, the cylindrical wall 122 of the flow directing element 120 can have an outer diameter that is greater than or equal to the diameter of the cavity 105.

The press-fit seal can help limit inadvertent flow out of the first flow path 126A and the second flow path 126B. For example, a tight fit between the flow directing element 120 and end plates 142, 144 of the first and second valve bodies 102, 104 can help limit blood from flowing between the first and second flow paths 126A, 126B and/or help limit blood from flowing from the first and second flow paths 126A, 126B to outer regions of the cavity 105. Similarly, the tight fit between the cylindrical wall 122 of the flow directing element 120 and the inner surfaces of the walls 146, 148 of the first and second valve bodies 102, 104 can help to prevent blood from leaking into the circumferential space around the flow directing element 120 in the event that blood escapes one of the flow paths 126A, 126B.

The pin 117, which extends radially outward from the cylindrical outer wall 122 of the flow directing element 120, is typically integrally molded with the cylindrical outer wall 122. Alternatively, the pin 117 can be attached to the cylindrical outer wall 122 using other suitable techniques. For example, the pin-like member 117 can be attached to the cylindrical outer wall 122 using fasteners (e.g., threaded fasteners), adhesive bonds, thermal bonds, or chemical bonds.

The first and second valve bodies 102, 104 and the flow directing element 120 are typically made of one or more biocompatible high-impact thermoplastic or thermoset materials. In some implementations, the valve bodies 102, 104 are formed of acrylic-based multipolymer compound (e.g., a biocompatible high impact MMA/styrene/acrylonitrile terpolymer or similar injection moldable thermoplastic compound). However, other medical grade materials, such as polycarbonate, polysulfone, or blends of these types of materials, can alternatively or additionally be used. The first and second valve bodies 102, 104 and the flow directing element 120 are typically formed using injection molding techniques. However, other techniques, such as etching and machining, can alternatively or additionally be used.

FIGS. 3 and 4 are cutaway perspective views illustrating the flow directing element 120 in a normal flow orientation and a reverse flow orientation, respectively. Portions of the cylindrical outer wall 122 of the flow directing element have been cutaway to provide a clear view of the twisted partition 124. As shown, the flow directing element 120 can be rotated within the cavity 105 to fluidly connect the different passages with one another to reverse fluid flow within the blood flow reversal valve 100. In particular, when the flow directing element 120 is in the normal flow orientation, as shown in FIG. 3, the partition 124 is positioned relative to the stationary fluid passages such that the axially aligned fluid passages 106, 110 are fluidly connected via the flow path 126A and the axially aligned fluid passages 108, 112 are fluidly connected via the flow path 126B. When the flow directing element 120 is in the reverse flow orientation, as shown in FIG. 4, the partition 124 is positioned relative to the stationary fluid passages such that the axially misaligned fluid passages 106, 112 are fluidly connected via the flow path 126B and the axially misaligned fluid passages 108, 110 are fluidly connected via the flow path 126A.

Figure 5:
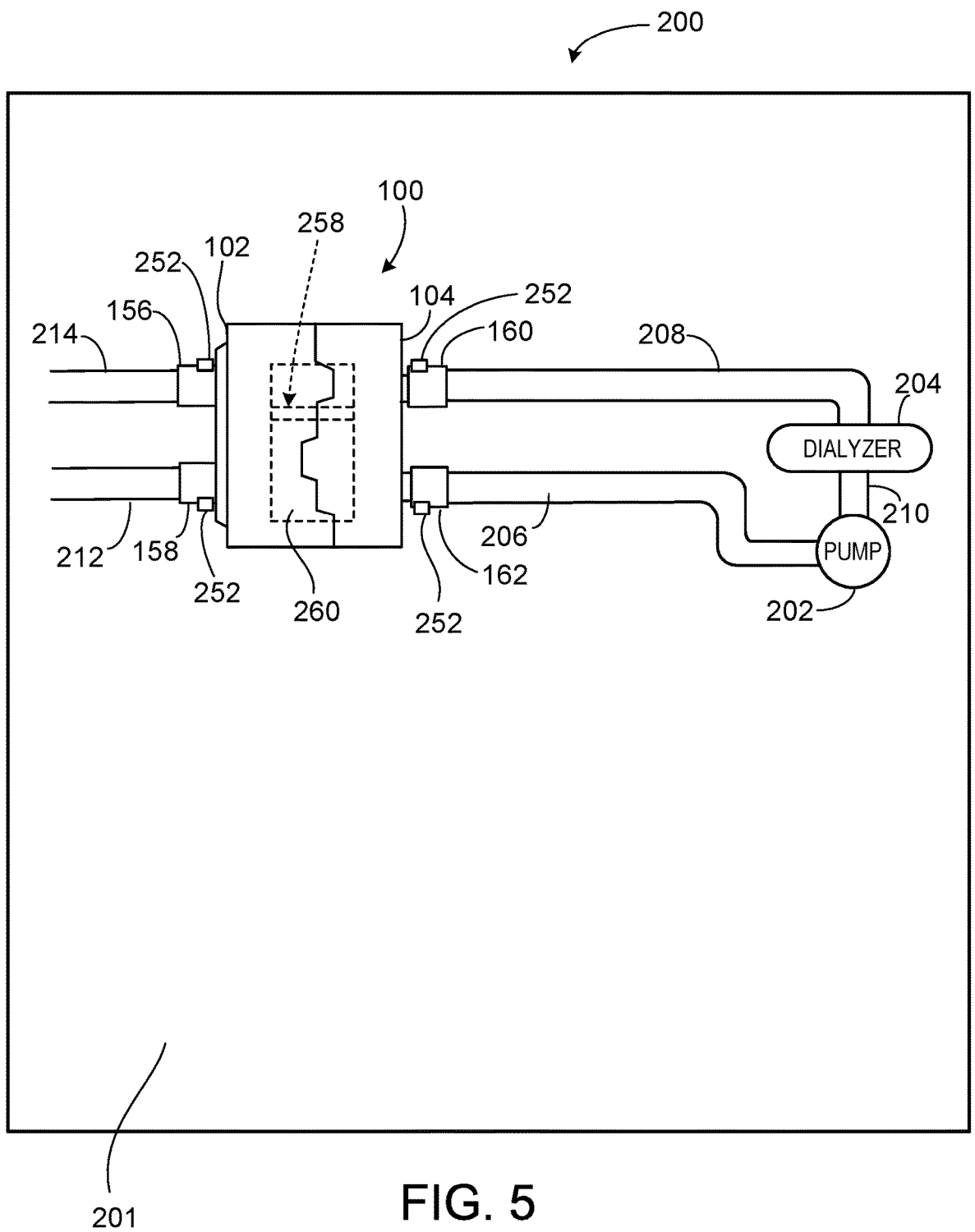
FIG. 5 is a schematic illustration of a hemodialysis system including an extracorporeal blood line set that includes the blood flow reversal valve of FIG. 1 and that is connected to a hemodialysis machine.

FIG. 5 schematically illustrates a hemodialysis system 200 including a blood line set that includes the blood flow reversal valve 100 connected to a hemodialysis machine 201. The blood flow reversal valve 100 is fitted to a valve receptacle 250 mounted along a front face of the hemodialysis machine 201. Arterial and venous blood lines 212 and 214 are connected to blood line connectors 158 and 156, respectively, of the first valve body 102, and outlet and inlet blood lines 206 and 208 are secured to blood line connectors 162 and 160, respectively, of the second valve body 104.

As shown in FIG. 5, the second valve body 104 is fluidly connected to a pump 202 via the outlet blood line 206 and is fluidly connected to a dialyzer 204 via the inlet blood line 208. The pump 202 is fluidly connected to the dialyzer 204 via a connection tube 210. On the opposite side of the valve 100, the arterial and venous blood lines 212, 214 are fluidly connected to the first valve body 102 and can be connected to a patient during treatment. During treatment, as will be discussed below, the flow directing element 120 of the valve 100 can be rotated to reverse blood flow within the arterial and venous blood lines 212, 214 without reversing operation of the blood pump 202 or twisting the lines 206, 208, 212, 214.

The blood lines 206, 208, 210, 212, and 214 can be any of various types of blood lines. In some embodiments, the blood lines are formed of one or more compliant materials, such as polyvinylchloride (PVC), Di(2-ethylhexyl) phthalate (DEHP), polyolifins, etc. However, other conventional blood line materials can alternatively or additionally be used.

The pump 202 can be any of various pumping devices capable of forcing blood through system 200. Examples of suitable pumping devices include peristaltic pumps, such as those available from Sarns, Inc. (Ann Arbor, Mich.).

The dialyzer 204 can include any of various dialyzers. Examples of suitable dialyzers include Fresenius Optiflux® series dialyzers.

Figure 6:
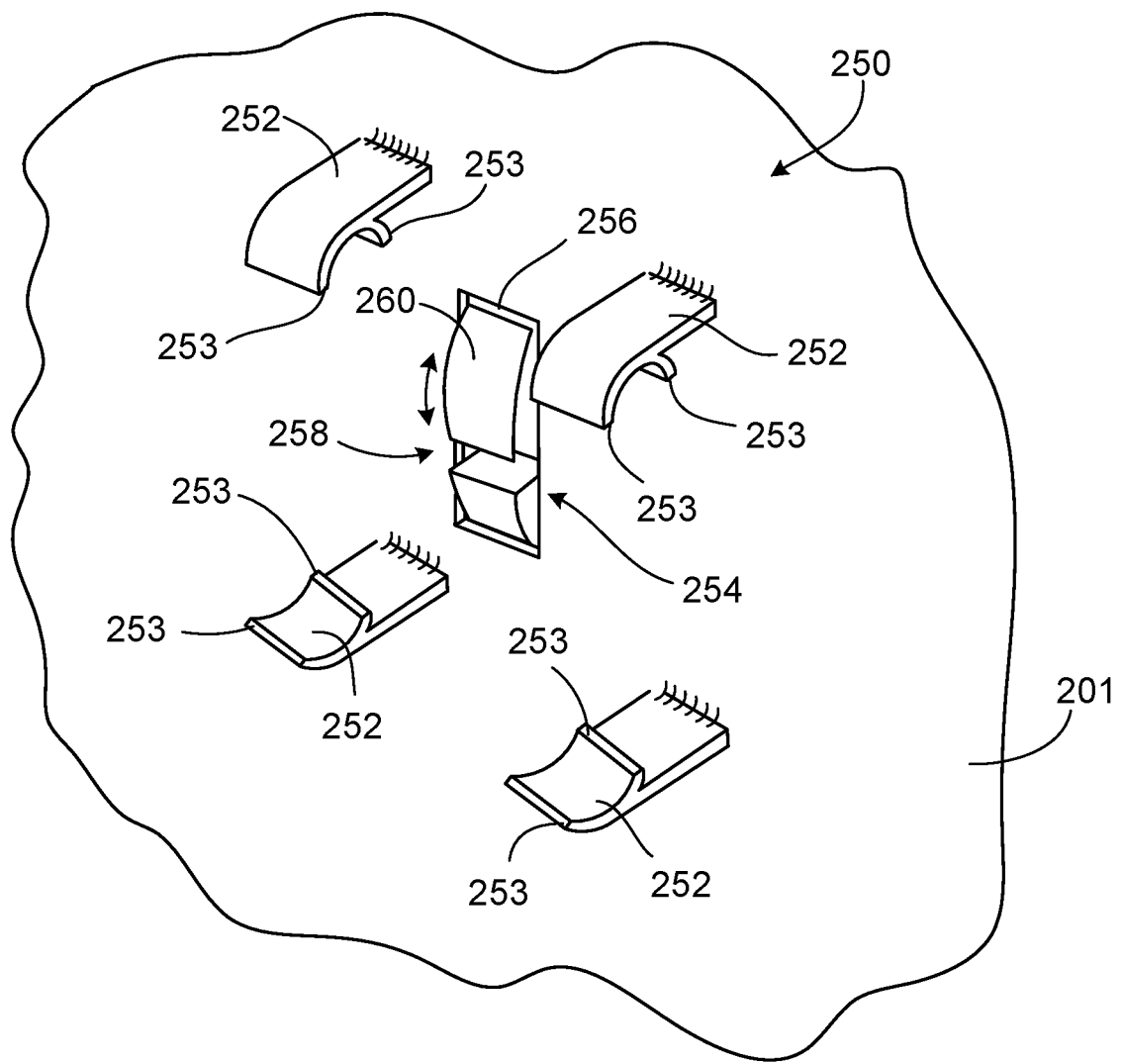
FIG. 6 is a perspective view of a valve receptacle of the hemodialysis machine of FIG. 5 without the blood flow reversal valve installed.

Referring to FIG. 6, the valve receptacle 250 includes valve retention elements (e.g., resilient fingers or clamping devices) 252 that are sized and configured grasp the blood flow reversal valve 100 during use. The valve retention elements 252 each have finger-like elements 253 that protrude inward towards a valve insertion area. The finger-like elements 253 are configured to grasp the blood line connectors 156, 158, 160, 162 and to help to keep the blood flow reversal valve 100 generally stationary during blood treatment and flow reversal.

A pin movement device or actuator 254 is located substantially in the center of the valve retention elements 252 and protrudes through a hole 256 formed in the face of the blood treatment machine. The actuator 254 has a pin slot 258 that is sized and configured to receive the pin 117 of the blood flow reversal valve 100. As shown, the actuator 254 is in the form of a rotating member 260 that, when rotated, can move the pin 117 relative to the stationary blood flow reversal valve 100. The rotating member 260 is connected to a motor (e.g., an electric motor) that can rotate the rotating member 260. As a result, the actuator 254 can move the flow directing element 120 and reverse the blood flow through the valve 100.

The hemodialysis machine 201 includes a controller (e.g., a microprocessor) that is electrically connected to the motor connected to the rotating member 260. Signals can be sent from the controller to the motor to operate the rotating member 260. The controller is also typically connected to a timer and/or sensors of the hemodialysis machine 201 so that the controller can receive signals from those components and operate the rotating member 260 based on the signals received from those components. In some implementations, the controller is programmed to transmit signals to rotate the rotating member 260 and thus reverse blood flow through the valve 100 at designated times during treatment. In such implementations, the controller can receive signals from the timer indicating how long the treatment has been underway and can cause the rotating member 260 to rotate when a predetermined time is reached. Alternatively or additionally, the controller can be programmed to rotate the rotating member 260 upon receiving signals indicating that readings of a sensor (e.g., a pressure sensor) are outside of a predetermined range.

Figure 7:
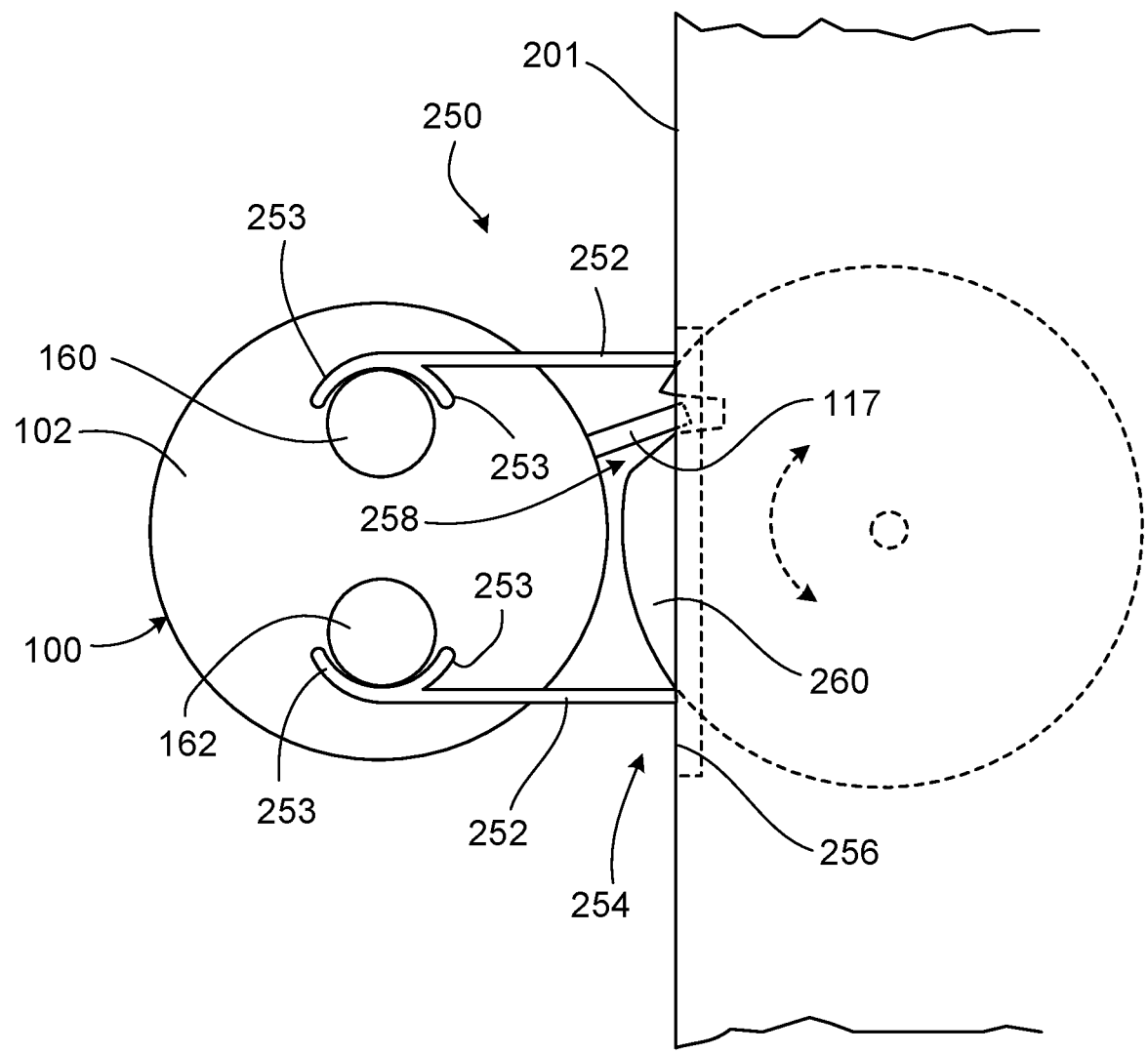
FIG. 7 is a schematic side view of the blood flow reversal valve of FIG. 1 mounted in the valve receptacle of the hemodialysis machine of FIG. 6.

FIG. 7 illustrates a schematic side view of the blood flow reversal valve 100 mounted in the valve receptacle 250. As shown, the blood line connectors 156, 158, 160, 162 are clipped into their associated valve retention elements 252 so that the blood flow reversal valve 100 is held generally stationary relative to the hemodialysis machine 201 during use. The pin 117 of the valve 100 is disposed in the pin slot 258 of the rotating member 260 so that the blood flow reversal valve 100 is engaged by the valve receptacle 250 for use.

Figure 8A:
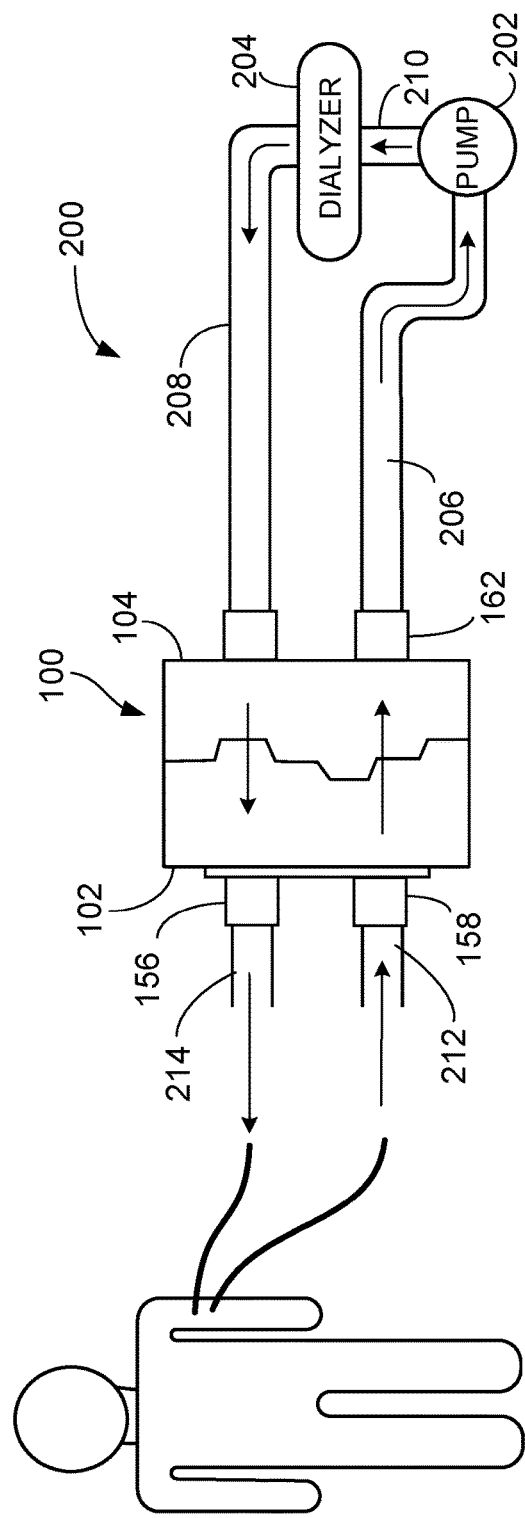
FIGS. 8A and 8B are schematic illustrations of blood flow through the blood flow reversal valve of FIG. 1 in its normal and reversed orientations, respectively.
Figure 8B:
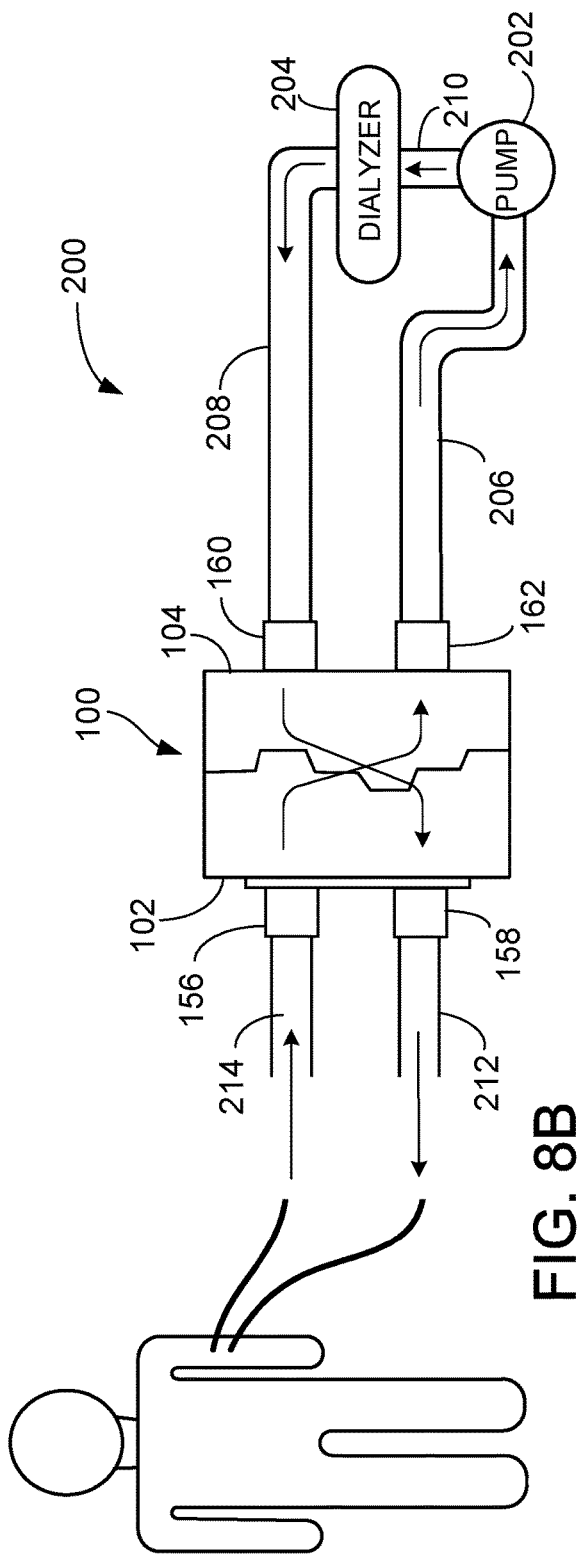

FIGS. 8A and 8B illustrate an exemplary method of using the hemodialysis system 200 to perform hemodialysis. Referring to FIG. 8A, the arterial and venous blood lines 212 and 214 are connected to an artery and vein, respectively, of a patient. Any of various known methods can be used to connect the arterial and venous blood lines 212 and 214 to the patient. For example, the blood lines 212 and 214 can be fluidly connected to a fistula, graft or shunt implanted within a patient, which connects a vein of the patient to an artery of the patient.

To begin treatment, the valve 100 is configured in the normal flow orientation in which the arterial blood line 212 is fluidly connected with the outlet blood line 206 via the second flow path 126B of the flow directing element 120 and the venous blood line 214 is fluidly connected with the inlet blood line 208 via the first flow path 126A of the flow directing element 120. When in this position, as discussed above, the pin 117 is aligned with the indicator 123, which displays the term "Normal," to inform the clinician that valve 100 is in the normal flow position. The blood pump 202 is then activated, causing blood to be drawn from the artery of the patient through the arterial blood line 212 and the outlet blood line 206 to the pump 202. The blood is then forced through the connection line 210 to the dialyzer 204, where the blood is filtered. After exiting the dialyzer 204, the blood continues through the inlet blood line 208 and the venous line 214 to the patient. The blood re-enters the vein of the patient via the venous line 214. The blood is generally pumped through the system 100 at a flow rate of approximately 300 ml/min. However, other flow rates are possible. The pump 202 can, for example, be configured to pump the blood at a rate of about 50 ml/min to about 600 ml/min.

As discussed above, it may be desirable at certain times during hemodialysis to reverse the flow of blood. Certain parameters can, for example, be measured in the standard flow and reversed flow configurations and compared to one another in order to determine the blood access flow rate. Examples of methods of determining blood access flow rates are described, for example, in U.S. Pat. Nos. 5,830,365 and 6,648,845, which are incorporated by reference herein.

When the dialysis system 200 determines that it is appropriate to reverse blood flow through the blood flow reversal valve 100, the pump 202 is typically briefly stopped. Once the blood flow has stopped, the controller of the dialysis system 200 sends a signal to rotating member 260 of the valve receptacle 250. The rotating member 260 is then rotated to move the pin slot 258 (i.e., to move the pin slot 258 downward in the orientation shown in FIG. 7) to move the pin 117. As the pin 117 moves from the normal flow position towards the reverse flow position, the partition 124 rotates within the blood flow reversal valve 100 toward a position in which it fluidly connects the fluid passages in a manner to induce a reserved flow.

After being placed in the reverse flow position illustrated in FIG. 8B, the arterial blood line 212 is fluidly connected with the inlet blood line 208 via the second flow path 126B of the flow directing element 120, and the venous blood line 214 is fluidly connected with the outlet blood line 206 via the first flow path 126A of the flow directing element 120. The pump 202 is then restarted, causing blood to be drawn from the vein of the patient and drawn through the venous blood line 214 and the outlet blood line 206 to the pump 202. The blood is then passed through the dialyzer 204 and flows through the inlet blood line 208. The blood then passes through the valve 100 to the arterial blood line 212. The blood re-enters the artery of the patient via the arterial blood line 212. During reversed flow, the pump 202 is operated in the same manner (i.e., the same direction) in which it is operated during normal flow. The pump 202 typically pumps blood at a rate of about 300 ml/min during reversed flow operation. However, other flow rates are possible. The pump 202 can, for example, be configured to pump the blood at a rate of about 50 ml/min to about 600 ml/min during periods of reversed blood flow.

After the desired period of reversed blood flow is completed, the pump 202 is again stopped and the flow directing element 120 is rotated back into the normal flow position. The pump 202 is then restarted, and the blood treatment is resumed.

While various embodiments have been described above, other embodiments are possible.

While the flow directing element 120 has been described as being press-fitted within the cavity 105 formed between the first and second valve bodies 102, 104 in order to create liquid-tight seals between the ends of the flow directing element 120 and the end plates 142, 144 of the first and second valve bodies 102, 104, other sealing techniques can alternatively or additionally be used. In some embodiments, for example, gaskets are attached to each axial end of the flow directing element 120. The gaskets can have a shape that corresponds to the shapes of the end surfaces of the flow directing element 120. For example, each of the gaskets can include an outer ring-shaped member and a central partition that extends through a central aperture of the ring-shaped member to form two semi-circular flow passages. The gaskets can be attached (e.g., adhesively attached, thermally bonded, chemically bonded, or over-molded) to the ends of the flow directing element 120 such that the fluid passages of the gaskets align with the flow paths 126A and 126B of the flow directing element 120. The gaskets are compressed between the ends of the flow directing element 120 and the end plates 142, 144 of the first and second valve bodies 102, 104 to form a liquid-tight seal between the ends of the flow directing element 120 and the end plates 142, 144 of the first and second valve bodies 102, 104. The gaskets can include one or more biocompatible materials that have a durometer of about 30 Shore D to about 40 Shore D (e.g., about 30 Shore D). Examples of materials from which the gaskets can be formed include polyisoprene latex, silicone, krayton, and blends of these types of materials.

In some implementations, the flow directing element (e.g., the cylindrical outer wall 122 and/or the partition 124) and/or the first valve body 102 and the second valve body 104 can include a fluid sealing element (e.g., an O-ring style sealing wiper, or other sealing elements) disposed along its edges to limit fluid from inadvertently flowing from the first and second flow paths.

In some implementations, one of the valve bodies includes a recessed slot portion that substantially defines the entire slot and the opposite valve body does not include a slot portion. Alternatively or additionally, the flow directing element can include other types of projections that allow the flow directing element to be moved within the blood flow reversal valve. For example, in some implementations, the flow directing element includes a region having teeth exposed within the slot that matingly engage teeth of a gear that is external to the blood flow reversal valve.

While the blood flow reversal valve state indicators 123, 125 have been described as being in the form of words applied to the first valve body, other types of indicators can be used for indicating the state of the blood flow reversal drive. For example, in some implementations, colored figures or suggestive symbols can be applied to indicate the state of the blood flow reversal valve. The indicators can alternatively or additionally be applied to other components of the blood flow reversal valve. For example, the indicators can be applied to the second valve body, or the indicators can be applied to portions of the flow directing element that become visible within slot when the flow directing element is rotated to the position associated with the particular indicator.

Figure 9:
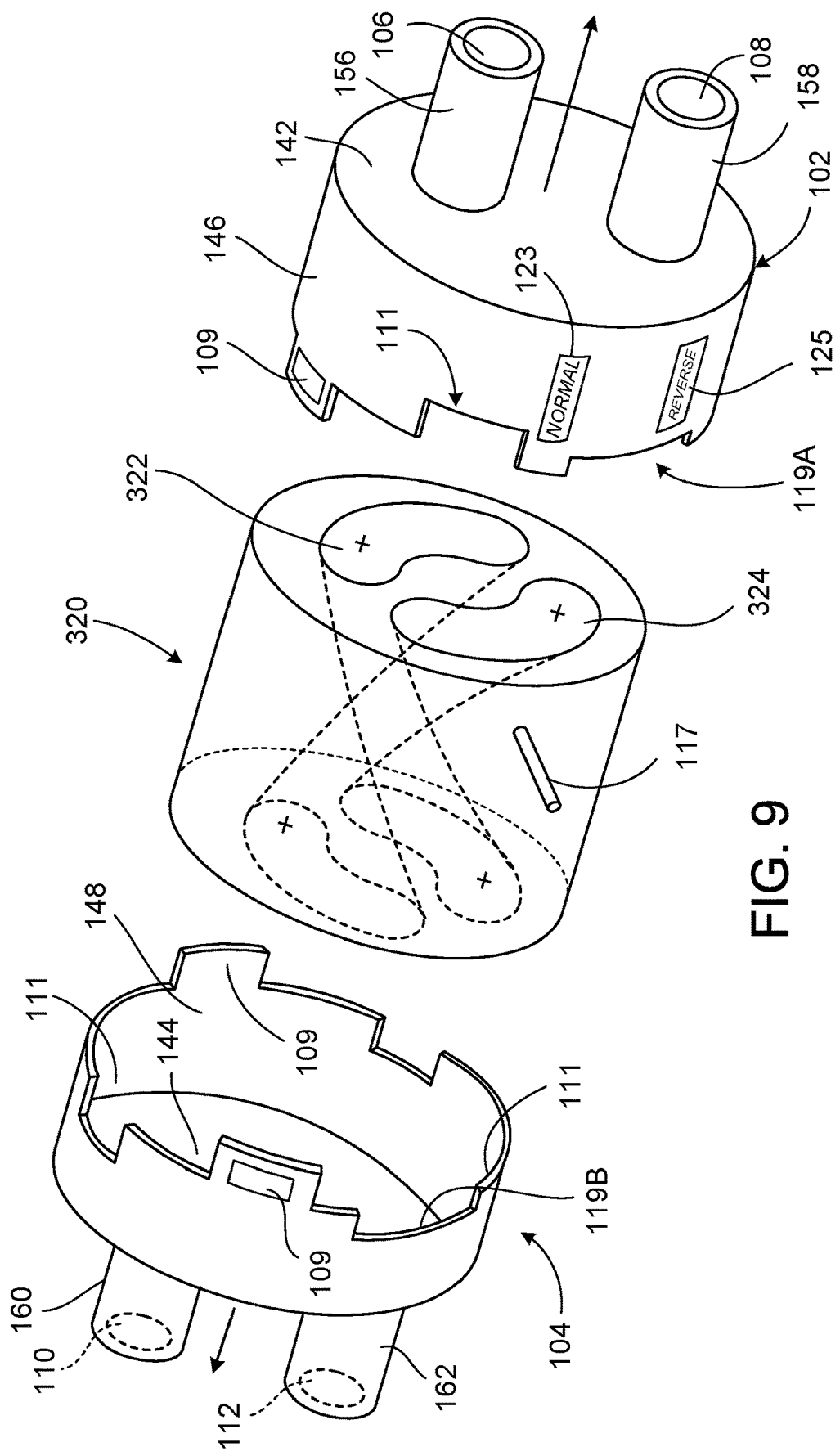
FIG. 9 is an exploded, perspective view of a blood flow reversal valve that includes a central flow directing element having kidney-shaped flow passages that helically curve through the flow directing element.

While the flow directing element 120 has generally been described as having a cylindrical cavity divided into two substantially half-circle shaped helical flow paths by the generally helical partition 124, other configurations are possible. FIG. 9, for example, is an exploded, perspective view of an alternative blood flow reversal valve 300 having a flow directing element 320 that includes two helical flow paths 322, 324. Each of the flow paths 322, 324 has a substantially curved cross-sectional shape (e.g., a kidney shaped cross-sectional area) that follows a substantially helical path through the flow directing element 320. The flow directing element 320 is disposed in the cavity 105 between the first and second valve bodies 102, 104 and is rotatable between a normal flow position and a reverse flow position to fluidly connect different fluid end plate passages 106, 108, 110, 112. The flow directing element 320 can be sealed within the cavity 105 using any of the various techniques described above with respect to the flow directing element 120.

The curved flow paths 322, 324 can improve fluid flow through the blood flow reversal valve 300, as well as reduce blood coagulation. The geometry and arrangement of the curved flow paths 322, 324 can also affect the angular distance that the flow directing element 320 needs to be rotated in order to reverse the flow though the blood flow reversal valve. The rotation angle by which the flow directing element 320 must be rotated to reverse the flow through the valve 300 depends on several factors including the axial length and twist angle of the flow paths 322, 324. The required rotation angle can typically be determined by subtracting the twist angle of the flow path from 180 degrees. Therefore, as the twist angle increases (and the span and size of the flow path 322 increases), the rotation angle needed to reverse the flow decreases. The flow paths 322, 324 are typically designed such that rotating the flow directing element 320 by about 5 degrees to about 180 degrees (e.g., about 60 degrees to about 120 degrees, about 90 degrees) about the longitudinal axis of the valve 300 is sufficient to reverse flow through the valve 300.

Figure 10:
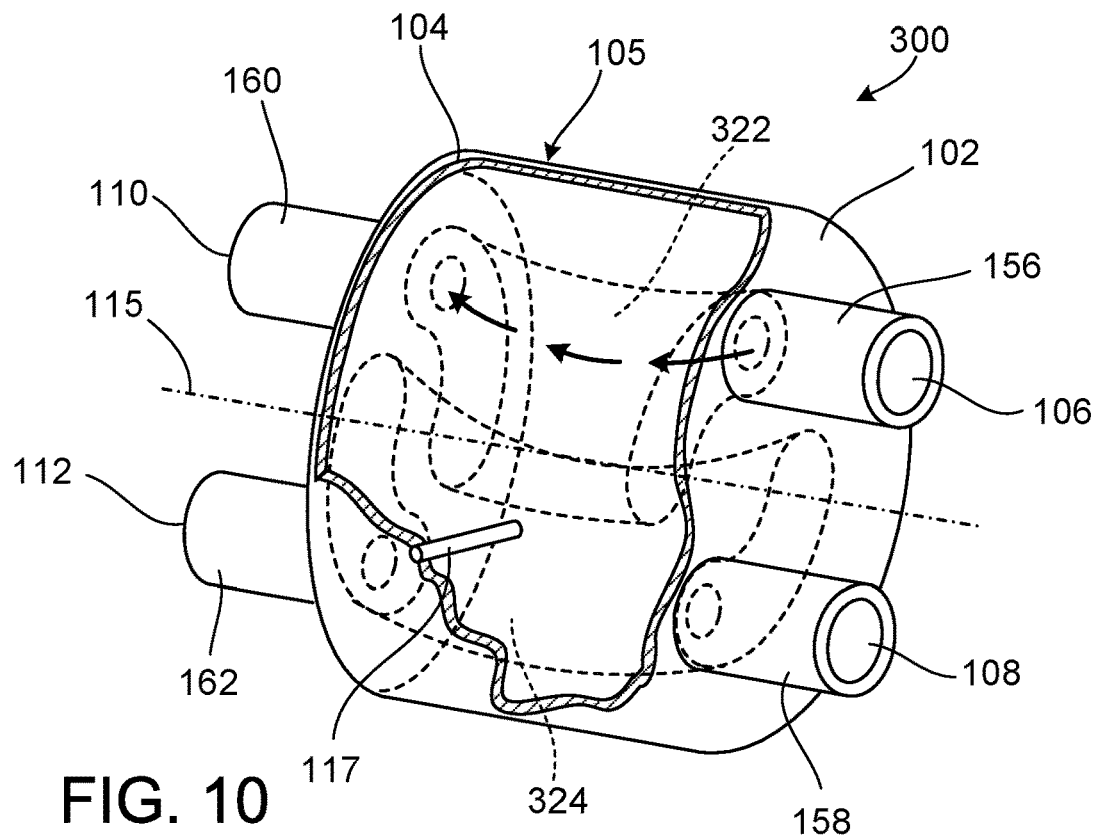
FIGS. 10 and 11 are cutaway, perspective views of the blood flow reversal valve of FIG. 9 with the central flow directing element in first and second positions, respectively, to direct blood flow in a normal direction and in a reverse direction, respectively.
Figure 11:
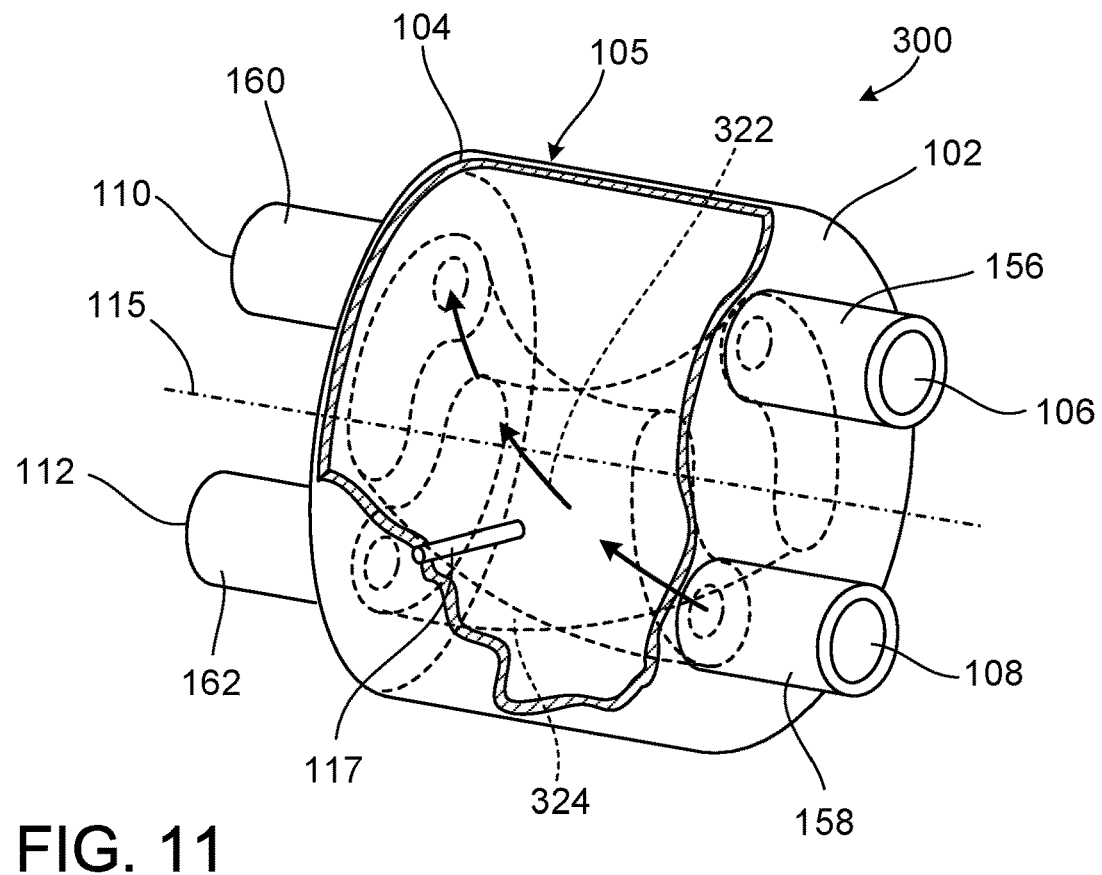

FIGS. 10 and 11 are cutaway perspective views that illustrate the different positions of the flow directing element 320 relative to the first and second valve bodies 102, 104. Referring to FIG. 10, when the flow directing element 320 is arranged in a first position (e.g., the normal flow position) relative to the first and second valve bodies 102, 104, the first flow path 322 fluidly connects the axially aligned fluid passages 106 and 110 and the second flow path 324 fluidly connects the axially aligned fluid passages 108 and 112. Referring to FIG. 11, when the flow directing element 320 is arranged in a second position (e.g., the reversed flow position) relative to the first and second valve bodies 102, 104, the first flow path 322 fluidly connects the axially misaligned fluid passages 108 and 110 and the second flow path 324 fluidly connects the axially misaligned fluid passages 106 and 112 to reverse the blood flow through the valve 300.

The valve 300 can be incorporated into a blood line set and connected to the hemodialysis machine 201 in the manner described above with respect to the valve 100. Thus, the actuator 254 can be used to automatically reverse blood flow through the valve 100 during treatment.

While the blood flow reversal valves 100, 330 include mating tabs and slots that are used to secure the valve bodies 102, 104 to one another, other devices or techniques can be used. For example, alternatively or in addition to interlocking tabs and slots, fasteners (e.g., threaded fasteners (e.g., bolts or screws), rivets, or other fasteners) can be used. In some implementations, one of the valve bodies includes a circumferentially formed recess or lip that is sized to receive and be engaged by a circumferentially formed resilient conical ring disposed around an adjoining edge or the other valve body. Using the circumferentially formed recess and ring, the two valve bodies can be pressed together and the ring can snap into the recess to secure the valve bodies together. In some implementations, the first and second valve bodies 102, 104 include threaded portions that permit them to be screwed to one another. In some implementations, separate devices, such as clamps can be used to press the first valve body 102 onto the second valve body 104.

While the actuator 254 of the hemodialysis machine 201 has been described as being rotatable, the actuator can alternatively include a vertically moveable element having a hole to receive the pin of the blood flow reversal valve. Alternatively or additionally, the valve retention element can include a moving gear configured to engage a mating gear mounted on the blood flow reversal valve to move the flow directing element.

While the blood lines have been described as being bonded to the blood line connectors using an adhesive, other techniques can be used. For example, the blood lines can be thermally bonded and/or chemically bonded to the blood line connectors. As another example, the blood lines and blood line connectors can include mating luer locking mechanisms that can be used to secure the blood lines to the blood line connectors.

While the blood flow reversal valve has been described as being used in combination with a dialysis machine that is able to automatically reverse the blood flow through the valve when desired, other configurations are possible. For example, in some implementations, a user (e.g., a clinician, patient, or other person administering a blood treatment process) manually moves the flow directing element (e.g., by grasping the projection extending radially from the flow directing element) from the normal flow position to the reversed flow position.

While the blood flow reversal valve has been described as a component for a hemodialysis system, the blood flow reversal valve can alternatively or additionally be used with other types of blood treatment systems where flow reversal is desired. Examples of other types of blood treatment systems include plasmapheresis, autotransfusion devices, and hemoabsorptive devices.

A number of embodiments have been described. Nevertheless, it will be understood that various modifications may be made without departing from the spirit and scope of the invention. Accordingly, other embodiments are within the scope of the following claims.

What is claimed is:

1. A method of reversing blood flow using a blood flow reversal valve that comprises a first member having a first passage and a second passage, a second member rotationally fixed relative to the first member and having a first passage and a second passage, and a flow directing element disposed in a cavity formed between the first and second members, the flow directing element comprising a planar member extending through a semi-helical path, the method comprising:

moving the flow directing element of the blood flow reversal valve from a first position in which the first passage of the first member and the first passage of the second member are fluidly connected and the second passage of the first member and the second passage of the second member are fluidly connected to a second position in which the first passage of the first member and the second passage of the second member are fluidly connected and the second passage of the first member and the first passage of the second member are fluidly connected, wherein the first and second members of the blood flow reversal valve remain fixed with respect to one another while the flow directing element moves from the first position to the second position.

2. The method of claim 1, wherein moving the flow directing element from the first position to the second position comprises rotating the flow directing element relative to first and second members.

3. The method of claim 1, wherein the flow directing element is moved from the first position to the second position by an actuator of a blood treatment machine.

4. The method of claim 3, further comprising transmitting a signal from a controller of the blood treatment machine to the actuator to move the flow directing element.

5. The method of claim 1, further comprising moving the flow directing element from the second position back to the first position.

6. The method of claim 1, further comprising running a blood pump to force blood through the blood flow reversal valve.

7. The method of claim 6, further comprising stopping the blood pump prior to rotating the flow directing element from the first position to the second position.

8. The method of claim 1, further comprising measuring one or more parameters of blood flowing through the blood flow reversal valve.

* * * * *